United States Patent [19]

Brokke et al.

[11] Patent Number: 4,524,214

[45] Date of Patent: Jun. 18, 1985

[54] PROCESS FOR FORMING ESTERS OF GLYOXYLIC ACIDS

[75] Inventors: Mervin E. Brokke, Stamford; Walter L. Magee, Jr., Danbury, both of Conn.

[73] Assignee: Stauffer Chemical Company, Dobbs Ferry, N.Y.

[21] Appl. No.: 548,375

[22] Filed: Nov. 3, 1983

[51] Int. Cl.$^3$ .............................................. C07C 69/76
[52] U.S. Cl. ...................................................... 560/51
[58] Field of Search ........................................... 560/51

[56] References Cited

U.S. PATENT DOCUMENTS 3,996,259 12/1976 Lee .................................. 260/465 B
4,417,053 11/1983 Corvers et al. ....................... 560/51

OTHER PUBLICATIONS

G. A. Lee, Tetrahedron Letters, No. 20, pp. 1641–1644, 1976.

Stevens et al., J. Org. Chem., 1980, 45, No. 10, 1980, pp. 2030–2032.

*Primary Examiner*—Paul J. Killos
*Attorney, Agent, or Firm*—Richard P. Fennelly

[57] ABSTRACT

Esters of glyoxylic acids are formed by the oxidation of an organoglycolate ester using a hypohalide oxidizing agent, preferably under phase transfer conditions using a phase transfer catalyst. An example of a suitable oxidizing agent is sodium hypohalite, and a preferred starting material is methyl mandelate.

12 Claims, No Drawings

PROCESS FOR FORMING ESTERS OF GLYOXYLIC ACIDS

BACKGROUND OF THE INVENTION

1. Field of the Invention

The present invention relates to a synthetic method for the formation of esters of glyoxylic acids. Such compounds find use as photoinitiator compounds or as intermediates in the synthesis of agricultural/pharmaceutical compounds.

2. Description of the Prior Art

Various processes have been described in the prior art for the formation of esters of glyoxylic acids. For example, U.S. Pat. No. 3,532,737 to J. E. Siggins relies upon esterification of the corresponding acids having the formula:

A process for forming esters of aryl glyoxylic acids by reaction of phenyl glyoxyoyl chloride with the appropriate alcohol is described in U.S. Pat. No. 4,024,297 to G. W. Gruber. U.S. Pat. No. 4,038,164 to F. A. Via describes formation of esters of glyoxylic acids by the reaction of methyloxalyl chloride with benzene in the presence of aluminum trichloride or by the oxidation of mandelic acid to phenyl glyoxylic acid and its subsequent esterification with methyl alcohol.

SUMMARY OF THE PRESENT INVENTION

The present invention relates to a process for the formation of esters of glyoxylic acids by the oxidation of an organoglycolic ester using a hypohalite oxidizing agent, if desired, under phase transfer conditions using a phase transfer catalyst.

DETAILED DESCRIPTION OF THE PRESENT INVENTION

The esters of glyoxylic acid which are the intended end product of the present invention are well known and are described in various prior art publications and patents. Examples of certain patents describing these types of compounds have been given before.

The esters of glyoxylic acid which are intended as end products of the present invention contain the desired glyoxylate ester structure, —C(O)—C(O)—OR, where R is an alkyl group having from about 1 to about 6 carbon atoms. This moiety is bonded to a suitable organic moiety, such as a heterocyclic, aryl of 6-14 carbon atoms or substituted phenyl group as indicated in U.S. Pat. No. 4,038,164 to F. A. Via. The starting material for the present invention in its broadest context is an organoglycolate ester which contains the structural unit —CH(OH)—C(O)—OR, where R is as defined above. This structure is bonded to the corresponding moiety described above.

In the present invention the starting material for the desired oxidation step, in a particularly preferred embodiment, is an alkyl ester of mandelic acid (dl-phenylglycolic acid, methyl ester). Such compounds have the formula:

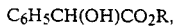

where R is an alkyl having from about 1 to about 6 carbon atoms. Compounds of this type are known and, if desired, can be formed by the reaction of an appropriate alcohol with mandelic acid under acidic conditions with reflux.

The oxidation of the organoglycolic ester, e.g., alkyl mandelate, by the hypohalite can be performed, if desired, by using a suitable organic liquid as the reaction medium. For example, methylene chloride, ethylene dichloride, diethylether, toluene, benzene are suitable solvents that can be used in the present invention, if desired. The organoglycolic ester is brought into contact with a suitable amount of hypohalite oxidizing agent, preferably in the form of an alkali metal hypochlorite solution in water. The amount of ester of glyoxylic acid and hypochlorite that can be employed in the present invention can be varied quite widely, i.e., from about 1:1 to about 1:10 if expressed on a molar ratio. After the hypohalite oxidizing agent, e.g. an alkali metal hypohalite such as sodium hypochlorite, and ester have been allowed to react for a sufficient amount of time, e.g., from about 2 to about 6 hours, the organic layer which contains the resulting glyoxylate compound of interest can be separated and can be dried and stripped to obtain the desired compound.

If desired, the reaction can be conducted using an appropriate phase transfer catalyst, if a solvent reaction medium is employed. Representative compounds which can be used as such catalysts are known, and include quaternary ammonium and phosphonium salts. The ammonium salts are preferred and such salts as benzyl trimethyl, benzyl triethyl, and tetrabutyl ammonium chlorides and bromides are representative catalysts of this type. The amount of catalysts that can be employed in the reaction is quite small and can range from about 0.01 to about 1% by weight of the reaction mixture.

The foregoing is intended to describe certain embodiments of the present invention but should not be construed in a limiting sense. The examples which follow illustrate certain embodiments of the present invention for illustration.

EXAMPLE 1

Methyl mandelate (1.0 gm.), methylene chloride (10.0 mls.) and a crystal of tetra-n-butyl ammonium bromide catalyst were mixed together in an Erlenmeyer flask using magnetic stirring. To this mixture was then added dropwise 50 mls. of a 5.25% sodium hypochlorite bleach solution (CLOROX brand). After three hours the organic layer was separated, dried over sodium sulfate, and stripped under vacuum. The residue was analyzed by infrared spectroscopy which showed peaks at 1740 and 1695 cm$^{-1}$ which are characteristic of methyl phenylglyoxylate and which are absent in methyl mandelate.

EXAMPLE 2

Example 1 was repeated with the exception that the tetra-n-butyl ammonium bromide was left out. After three hours, infrared analysis of the organic phase showed that the reaction was 80% complete.

EXAMPLE 3

Methyl phenylglyoxylate was produced in accordance with the general procedure shown in Example 1 by reacting the following:

| Ingredient | Amount |
| --- | --- |
| Methyl mandelate | 10 gm. |
| Methylene chloride | 100 mls. |
| Tetra-n-butylammonium bromide | Pinch |
| Sodium hypohalite solution | 100 mls. |

| Ingredient | Amount |
|---|---|
| (5.25%) - CLOROX brand | |

The reaction mixture was cooled slightly in an ice bath. The reaction was judged completed after about twenty-five minutes, and the yield of crude product was 9.7 gm.

EXAMPLE 4

Melted methyl mandelate (225.3 gm. 1.35 moles) was dissolved in 500 ml. of methylene chloride and washed with aqueous sodium bicarbonate to remove residual sulfuric acid from the preparation of the mandelate. A 0.5 gm. portion of tetra-n-butylammonium bromide was then added to the methylene chloride solution. Oxidation took place in two stages and was monitored by IR spectroscopy.

A total of 2.5L of 5.25% NaOCl solution was added, in varying portions, over 3.8 hrs. while maintaining a pot temperature of 24°–32° C. Another 0.5 gm. of Bu$_4$NBr was added in the last 80 min. of this period.

The aqueous phase was then replaced with two 250 ml. portions of fresh NaOCl solution added over 30 min. The pot temperature was maintained at 22°–33° C. After that time, reaction was judged complete, and the solvent was distilled in a rotary evaporator. High vacuum distillation provided 178.3 gm. (1.08 moles, 80% yield) of methyl phenylglyoxylate.

The foregoing Examples are given to illustrate certain embodiments of the present invention and should not be construed in a limiting sense. The scope of protection sought is given in the claims which follow.

What is claimed:

1. A process for the formation of an ester of a glyoxylic acid which comprises oxidizing an organoglycolic ester with hypohalite oxidizing agent.
2. A process as claimed in claim 1 wherein the oxidation is conducted under phase transfer conditions using a phase transfer catalyst.
3. A process as claimed in claim 1 wherein the hypohalite oxidizing agent is an alkali metal hypohalite oxidizing agent.
4. A process as claimed in claim 1 wherein the molar ratio of ester of glycolic acid to hypohalite oxidizing agent ranges from about 1:1 to about 1:10.
5. A process as claimed in claim 1 wherein the ester of the glycolic acid which is oxidized is an ester of mandelic acid.
6. A process as claimed in claim 5 wherein the oxidation is conducted under phase transfer conditions using a phase transfer catalyst.
7. A process as claimed in claim 5 wherein the hypohalite oxidizing agent is an alkali hypohalite oxidizing agent.
8. A process as claimed in claim 5 wherein the molar ratio of ester of glycolic acid to hypohalite oxidizing agent ranges from about 1:1 to about 1:10.
9. A process as claimed in claim 5 wherein the ester of the glycolic acid which is oxidized is an ester of mandelic acid.
10. A process as claimed in claim 5 wherein the oxidation is conducted using an alkyl ester of mandelic acid as the ester of the glycolic acid and sodium hypochlorite as the oxidizing agent.
11. A process as claimed in claim 10 in which the reaction is conducted under phase transfer conditions using a solvent and a quaternary ammonium phase transfer catalyst.
12. A process as claimed in claim 10 wherein methyl phenyl glyoxylate is formed as the product.

* * * * *